Figure 1:
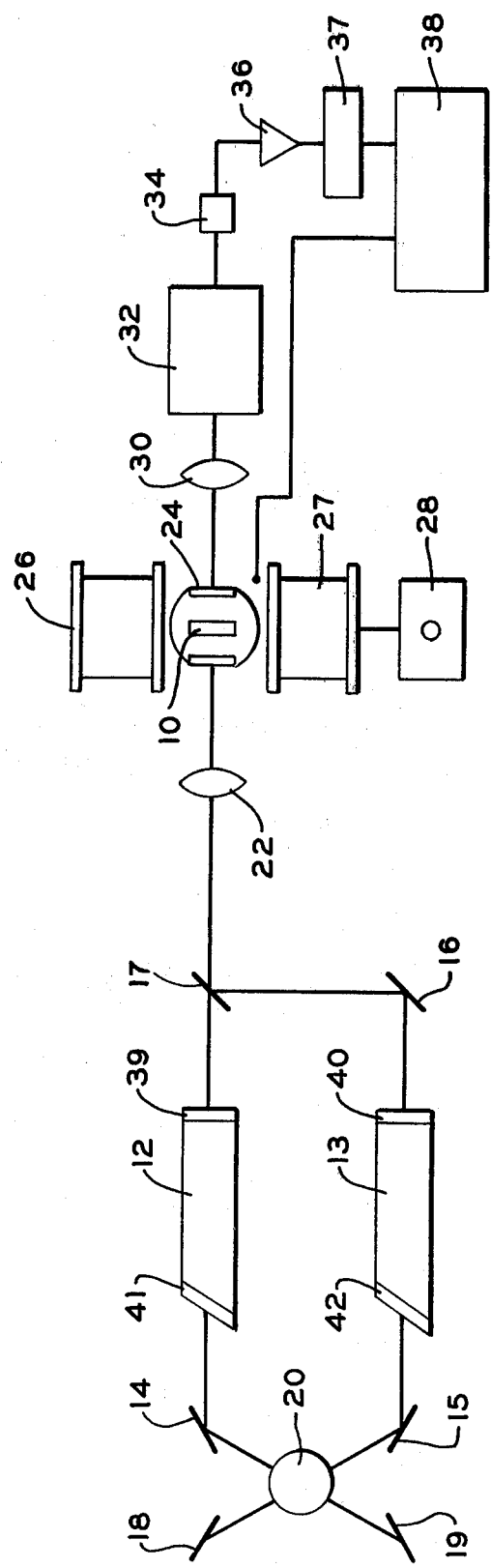

United States Patent [19]

Khan et al.

[11] 4,316,147
[45] Feb. 16, 1982

[54] APPARATUS FOR DETERMINING THE COMPOSITION OF MERCURY-CADMIUM-TELLURIDE AND OTHER ALLOY SEMICONDUCTORS

[75] Inventors: Muhammad A. Khan, Bloomington; Paul W. Kruse, Jr.; John F. Ready, both of Edina, all of Minn.

[73] Assignee: Honeywell Inc., Minneapolis, Minn.

[21] Appl. No.: 126,633

[22] Filed: Mar. 3, 1980

[51] Int. Cl.³ ............................................. G01N 27/00
[52] U.S. Cl. ...................................... 324/300; 324/304
[58] Field of Search ............... 324/300, 304, 305, 316, 324/77 K, 71 SN

[56] References Cited

U.S. PATENT DOCUMENTS 3,984,802 10/1976 Lippel et al. ...................... 324/77 K
4,147,974  4/1979 Greenwood ........................ 324/304

Primary Examiner—Michael J. Tokar
Attorney, Agent, or Firm—Omund R. Dahle; Laurence J. Marhoefer

[57] ABSTRACT

Apparatus for determining the composition of mercury-cadmium-telluride or other alloy semiconductors by using a four-photon mixing phenomenon. Means are provided for a pair of colinear laser beams of different optical frequencies such that the colinear beams passed through a sample of $Hg_{1-x}Cd_xTe$ or other alloy semiconductors to produce emissions beams of the original incident optical frequencies and two or more additional optical frequencies formed by an electron spin-flip interaction. A magnetic field means is employed for varying a magnetic field across the sample during passage of the colinear beam from the points substantially below to substantially above the resonant field of the sample to produce a spin-flip signal which has a peak amplitude. Detector means are adapted to receive the emission beams to identify the spin-flip signal peak from which the spin-level splitting factor can be measured. Upon measurement of the spin-level splitting factor, the value for x can be calculated in $Hg_{1-x}Cd_xTe$ or other alloy semiconductor.

10 Claims, 3 Drawing Figures

APPARATUS FOR DETERMINING THE COMPOSITION OF MERCURY-CADMIUM-TELLURIDE AND OTHER ALLOY SEMICONDUCTORS

In an alloy semiconductor such as $Hg_{1-x}Cd_xTe$, the composition or value of x in the formula varies from point to point because of the extreme difficulty in controlling the composition during the growing process in which the crystal is formed. Because the electrical and optical properties vary with the composition, it is necessary to determine the composition in order to select those regions from which devices such as infrared detectors can be prepared.

Various suggestions have been made for quickly and conveniently identifying the chemical composition of alloy semiconductors such as $Hg_{1-x}Cd_xTe$. A density method may be employed, but this method requires cutting up the sample and its sensitivity becomes poor for small sample volumes. Electron-beam microprobe analysis has been found to be inaccurate and insensitive. Analytical wet chemistry is destructive. It and x-ray lattice constant measurements are insensitive.

Accordingly, it would be of great advantage to the alloy semiconductor art, including $Hg_{1-x}Cd_xTe$, if a method for non-destructively measuring the precise value of composition (x-value) could be obtained. It would be of an advantage if the measurement system used a relatively small volume. A preferred object of the present invention is to provide a device for measuring a property of the semiconductor, such as the spin level splitting factor, which is uniquely and fundamentally related to the energy gap. Then there would be no ambiguity, no need of calibration on a day-to-day basis.

It is, accordingly, a principal object of the present invention to provide a very accurate and highly sensitive method of determining the composition of alloy semiconductors in a non-destructive manner.

THE INVENTION

It has now been discovered that the above and other objects of the present invention can be accomplished in the following manner. Specifically, apparatus for determining the composition of a quantity of $Hg_{1-x}Cd_xTe$ (or other alloy semiconductors) has been discovered as set forth herein. It is based upon a nonlinear optical effect known as four-photon mixing (also referred to as four-wave mixing). The apparatus includes means for producing a pair of colinear laser beams at different optical frequencies. The apparatus includes means for positioning a sample of $Hg_{1-x}Cd_xTe$ (or other alloy semiconductors) along with means for directing the colinear laser beams on to the sample for passage through the sample. Interaction of these incident beams with the free electrons within the sample, arising from what is termed an "electron spin-flip," causes the production of radiation at two new optical frequencies, which is emitted from the sample. Magnetic field means are provided for producing a magnetic field at the position of the sample and for varying the value of the magnetic field from substantially below to substantially above the resonant field at which the intensity of the emitted radiation is maximized. Finally, detector means for receiving said emission beams are provided to identify the spin-flip signal peak from which the spin-level splitting factor g can be measured. Once the spin-level splitting factor has been measured, the value of x in the formula can be calculated as hereinafter described.

Four-photon mixing is a nonlinear optical effect which is exhibited within semiconductors when two laser beams of differing optical frequencies are incident at the same spot. The technique described herein involves four-photon mixing by the free electron spins, as opposed to the bound electrons.

Figure 2:
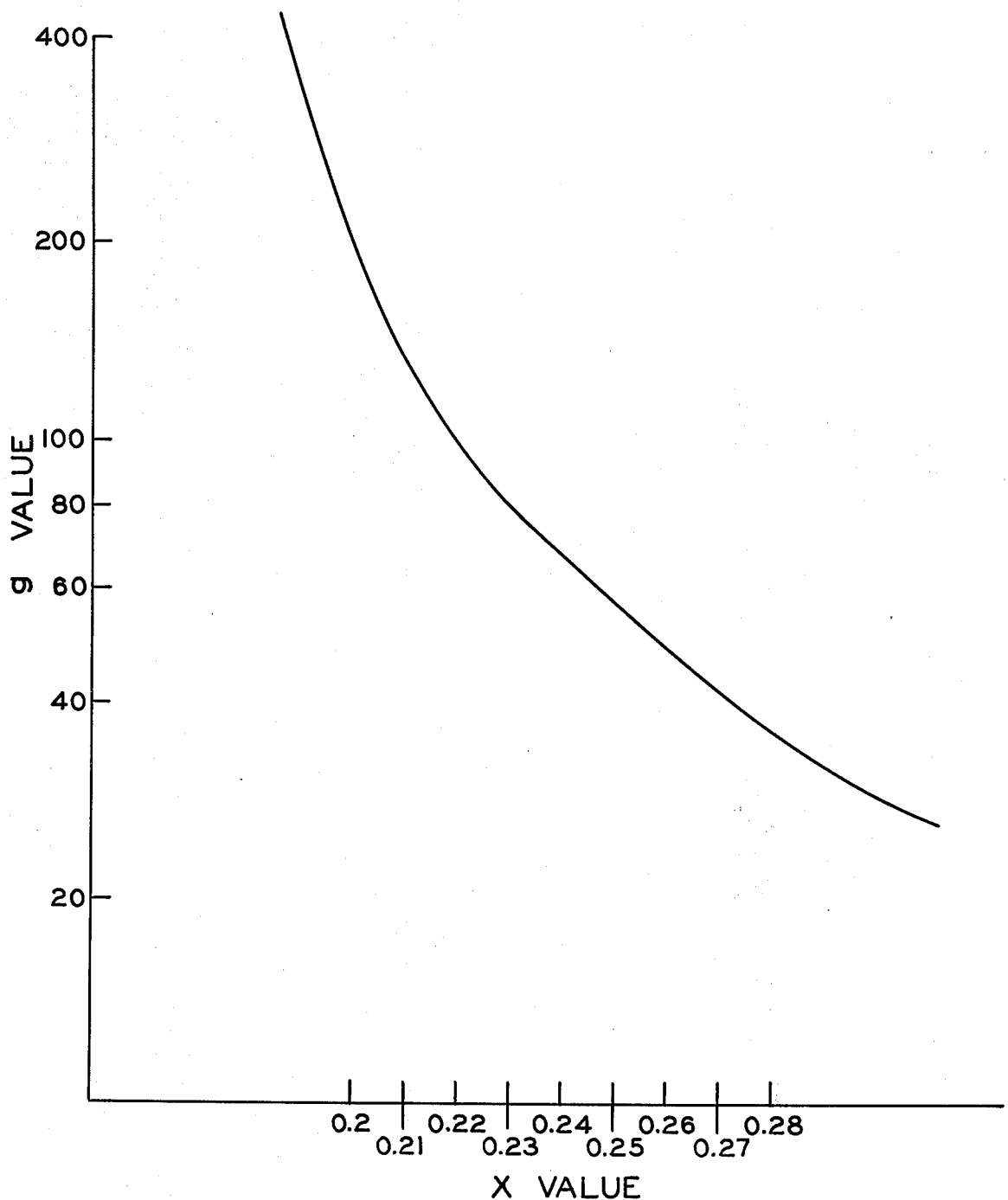
Figure 3:
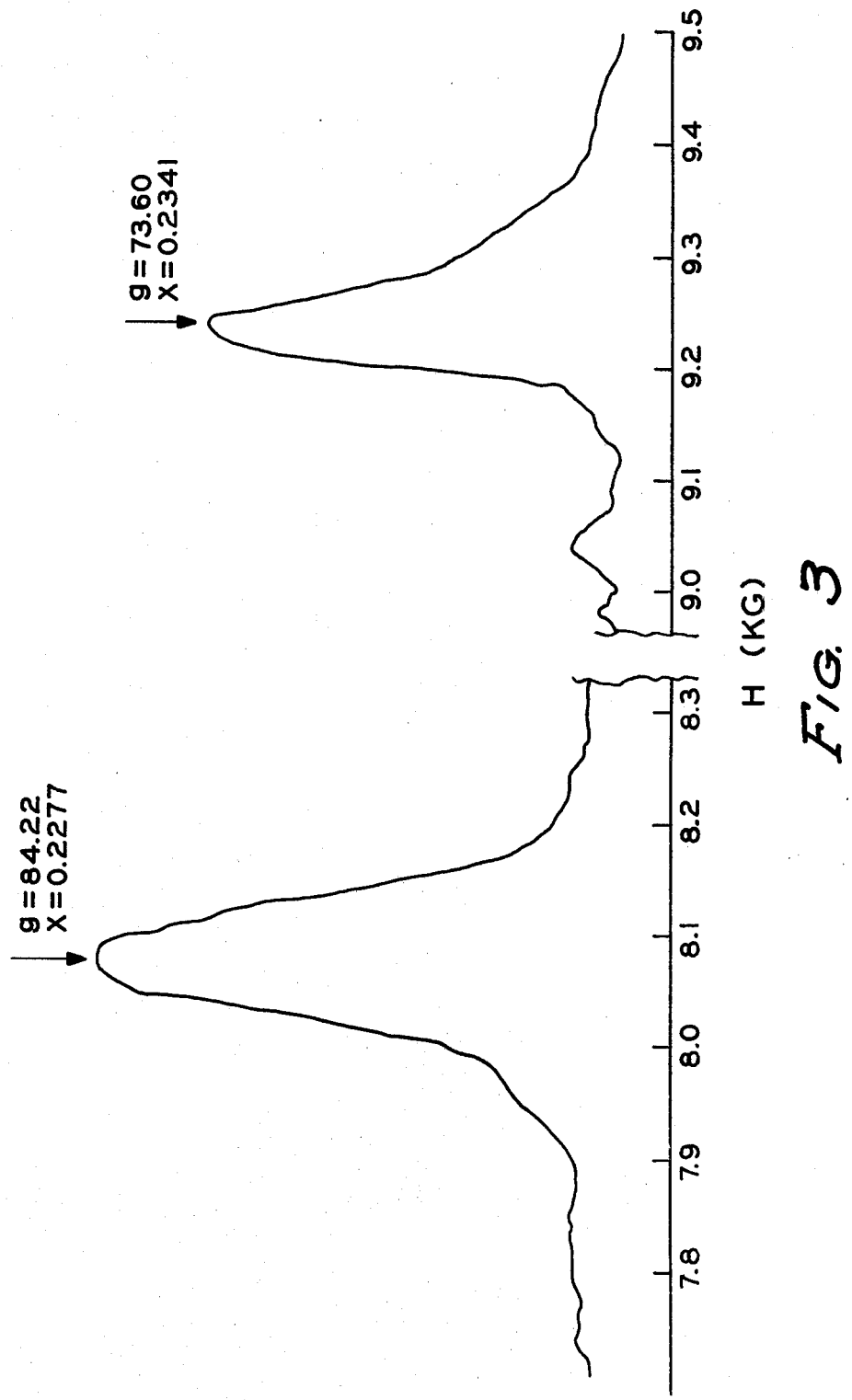

For a more complete understanding of the invention reference is hereby made to the drawings in which:

FIG. 1 is a schematic diagram showing the preferred embodiment of this present invention;

FIG. 2 is a curve showing the dependence of the spin-level splitting factor g on the value of x in the formula for $Hg_{1-x}Cd_xTe$; and, FIG. 3 is a graph showing two spin-flip signal peaks, one from each of two regions of different x value in $Hg_{1-x}Cd_xTe$, caused by sweeping a magnetic field from below the resonance peak to above that peak, thereby permitting measurement of g and calculation of x.

The apparatus described below is typical. Other experimental arrangements can also be made.

As shown in FIG. 1, a pair of $CO_2$ Q-switched lasers consisting of gas discharge tubes 12 and 13, stationary mirrors 14 and 15, end reflectors 39 and 40, rotating Q-switch mirror 20, and diffraction gratings 18 and 19, produce a pair of optical frequencies $\omega_1$ and $\omega_2$ which are made to be colinear by mirror 16 and beam mixer 17. (The embodiment of this invention can also be carried out with a continuous wave $CO_2$ laser). A lens 22 is employed to focus the beams on one flat surface of the mercury-cadmium-telluride (or other alloy semiconductor) sample 10 which is mounted normal to the beam. The sample 10 is contained in an optical dewar 24, preferably at a reduced temperature of approximately 10 degrees K or less, although the effect can be achieved at a substantially higher temperature. The dewar 24 is placed between the pole faces of an electromagnetic means 26 and 27. Brewster windows 41 and 42 are employed on the lasers such that one of the lasers is polarized parallel to the H-vector of the magnetic field and the other laser is polarized perpendicular to the H-vector of the magnetic field. From the back of the sample 10 opposite the incident region are emitted four colinear beams at frequencies $\omega_1$, $\omega_2$, $\omega_3$ which is $2\omega_1 - \omega_2$, and $\omega_4$ which is $2\omega_2 - \omega_1$. These four beams pass through lens 30 into a spectrometer 32 which is set to pass only $\omega_3$ or $\omega_4$. For the purposes of example, $\omega_4$ is passed in FIG. 1 through the spectrometer 32 to an infrared detector 34 which includes an amplifier 36, boxcar integrator 37 and an XY recorder 38. The gating signal to the boxcar integrator is provided by the output from a silicon photocell which senses the beam from a helium-neon laser reflected from the rotating mirror (not shown in FIG. 1). A magnetic field sensor 43 drives one axis of the XY recorder. When the magnetic field between magnet pole faces 26 and 27 is swept from zero or some low value substantially below the electron spin-flip resonance field of the $Hg_{1-x}Cd_xTe$ to a value substantially above the resonance field of the sample through means of control 28, the magnetic field passes through the resonance field peak and the detected signal rises, peaks and then falls. FIG. 3 represents this phenomenon of identifying a resonant peak at two different regions on a sample of mercury-cadmium-telluride. The resonance field H is given by the formula $H = (\omega_1 - \omega_2)\hbar/\mu g$ where $\hbar$ is Planck's constant divided by $2\pi$, $\mu$ is the Bohr magneton and g is the spin-level splitting factor. The splitting factor g is the parameter which is directly measured by this experiment. It is dependent upon x through a relationship which can be both theoretically and experimentally determined. FIG. 2 illustrates the dependence of g upon x for $Hg_{1-x}Cd_xTe$. The dependence would be different for a different alloy semiconductor.

Once the value of g has been measured, the value of x in the formula for mercury-cadmium-telluride can be calculated from FIG. 2. An analytical expression for FIG. 2 is:

$$g = \frac{19.771234}{5.295867x - 0.970909}.$$

A different expression would apply to a different alloy semiconductor. Thus, it can be seen that a highly practical method for determining the composition of mercury-cadmium-telluride or any other alloy semiconductor has been provided. As shown in FIG. 3, varying the magnetic field at the sample as the colinear beams impinge provides a signal peak such that the value of the magnetic field at the peak is directly related to the value of g in the irradiated region. In the experiments which produced the data shown in FIG. 3, two different regions on the sample have different values of x and have different values for g and thus produced peaks at different values for H. Calculation of the value of x is now possible from the known measured value of g.

It should be realized that similar but higher order nonlinear optical effects, e.g., resonant six-photon mixing, can be employed in the same way to determine the composition.

Having thus described the invention what is claimed is:

1. Apparatus for determining the composition of a quantity of mercury-cadmium-telluride, comprising:
    means for producing a pair of colinear laser beams of different frequencies:
    means for positioning a sample of mercury-cadmium-telluride having the formula $Hg_{1-x}Cd_xTe$;
    means directing said beams onto said sample for passage therethrough to produce an emission beam resulting from four-photon mixing;
    magnetic field means for producing a magnetic field at said sample and for varying the magnetic field from substantially below to substantially above the resonance field of said sample to produce a four-photon mixing signal having a peak;
    and, detector means receiving said emission beams to identify the resonance signal peak from which the spin-level splitting factor can be measured.

2. The apparatus of claim 1 wherein said means for producing a pair of colinear laser beams of different frequencies includes a pair of laser beam sources, a common Q-switching rotating mirror to synchronize the laser output pulses, mirror means for directing said two beams to be colinear and Brewster windows for polarizing said beams orthogonally.

3. The apparatus of claim 2 wherein said means for producing the pair of colinear laser beams are two $CO_2$ lasers.

4. The apparatus of claim 1 wherein said means for positioning a sample of mercury-cadmium-telluride includes Dewar means for holding said sample at a constant temperature, said Dewar means positioning said sample as to present to said laser beams one face of said crystal in a plane perpendicular to the path of said beams.

5. The apparatus of claim 1 wherein said detector means includes display means and spectrometer means for receiving said emission beams, said spectrometer means being adapted to pass only one beam, that beam being generated by passage through said sample and having a frequency of twice of one of the original frequencies minus the other original frequency, said spectrometer means further being adapted to direct said one beam onto said display means.

6. The apparatus of claim 5 wherein said display means includes recorder means to record the resonance field as a magnetic field means operates.

7. A method of determining the composition of a quantity of mercury-cadmium-telluride, comprising the steps of:
    four-photon mixing a pair of laser beams having different optical frequencies on a mercury-cadmium-telluride sample having the formula $Hg_{1-x}Cd_xTe$;
    measuring the spin-level splitting factor; and,
    calculating the value of x from the value of the spin-level splitting factor.

8. A method of determining the composition of a quantity of mercury-cadmium-telluride, comprising the steps of:
    beam mixing a pair of laser beams to render said beams colinear;
    directing said colinear beams to an optical Dewar containing said mercury-cadmium-telluride;
    subjecting said Dewar to a magnetic field swept from substantially below to substantially above the resonance field;
    measuring the spin-level splitting factor; and,
    calculating x in the formula $Hg_{1-x}Cd_xTe$ from the value of g and the known dependence of g upon x.

9. Apparatus for determining the composition of a quantity of alloy semiconductors, comprising:
    means for producing a pair of colinear laser beams of different frequencies:
    means for positioning a sample of alloy semiconductor; p1 means directing said beams onto said sample for passage therethrough to produce an emission beam resulting from four-photon mixing;
    magnetic field means for producing a magnetic field at said sample and for varying the magnetic field from substantially below to substantially above the resonance field of said sample to produce a four-photon mixing signal having a peak;
    and, detector means receiving said emission beams to identify the resonance signal peak from which the spin-level splitting factor can be measured.

10. A method of determining the composition of a quantity of alloy semiconductor, comprising the steps of:
    four-photon mixing a pair of laser beams having different optical frequencies on an alloy semiconductor sample;
    measuring the spin-level splitting factor; and,
    calculating the composition from the negative value of the spin-level splitting factor.

* * * * *